US010321963B2

(12) United States Patent
Comber et al.

(10) Patent No.: US 10,321,963 B2
(45) Date of Patent: Jun. 18, 2019

(54) APPARATUS AND METHOD FOR MOVING AN ELONGATE ROD

(71) Applicant: Vanderbilt University, Nashville, TN (US)

(72) Inventors: David B. Comber, Nashville, TN (US); Eric J. Barth, Nashville, TN (US); Jonathon E. Slightam, Milwaukee, WI (US); Vito Russel Gervasi, Pewaukee, WI (US)

(73) Assignee: VANDERBILT UNIVERSITY, Nashville, TN (US)

( * ) Notice: Subject to any disclaimer, the term of this patent is extended or adjusted under 35 U.S.C. 154(b) by 495 days.

(21) Appl. No.: 15/228,168

(22) Filed: Aug. 4, 2016

(65) Prior Publication Data

US 2017/0036883 A1 Feb. 9, 2017

Related U.S. Application Data

(60) Provisional application No. 62/200,712, filed on Aug. 4, 2015.

(51) Int. Cl.
A61B 34/30 (2016.01)
A61B 17/32 (2006.01)
(Continued)

(52) U.S. Cl.
CPC .......... *A61B 34/30* (2016.02); *A61B 10/0275* (2013.01); *A61B 17/0469* (2013.01);
(Continued)

(58) Field of Classification Search
CPC .............. A61B 17/32002; A61B 17/32; A61B 17/3423; A61B 17/0218; A61B 17/0483;
(Continued)

(56) References Cited

U.S. PATENT DOCUMENTS 4,316,465 A * 2/1982 Dotson, Jr. ......... A61F 9/00763
433/121
4,723,545 A * 2/1988 Nixon ............ A61B 17/320016
600/568

(Continued)

OTHER PUBLICATIONS

Wilson, J.F., "Mechanics of Bellows: A Critical Survey," Int. J. Mech. Sci. vol. 26, No. 11/12, pp. 593-605, 1984.

(Continued)

Primary Examiner — Scott A Smith
(74) Attorney, Agent, or Firm — Tarolli, Sundheim, Covell & Tummino LLP

(57) ABSTRACT

An apparatus for moving an elongate rod longitudinally and rotationally, and a method of moving the elongate rod longitudinally and rotationally, are provided. A translation member has a first translation member end held relatively stationary and a longitudinally spaced second translation member end which is selectively movable longitudinally with respect to the first translation member end via actuation of the translation member. The second translation member end is operatively connected to selectively impart longitudinal motion to the elongate rod. A rotation member has a first rotation member end held relatively stationary and a longitudinally spaced second rotation member end which is selectively rotatable with respect to the first rotation member end via actuation of the rotation member. The second rotation member end is operatively connected to selectively impart rotational motion to the elongate rod.

39 Claims, 11 Drawing Sheets

(51) Int. Cl.
   *A61B 10/02* (2006.01)
   *A61B 17/04* (2006.01)
   *A61B 34/00* (2016.01)
   *A61B 17/00* (2006.01)
   *A61M 25/01* (2006.01)
   *A61B 17/22* (2006.01)
   *A61B 90/00* (2016.01)
   *A61B 17/34* (2006.01)

(52) U.S. Cl.
   CPC ........ *A61B 17/32002* (2013.01); *A61B 34/70* (2016.02); *A61B 17/3423* (2013.01); *A61B 2010/0208* (2013.01); *A61B 2017/00292* (2013.01); *A61B 2017/00398* (2013.01); *A61B 2017/00539* (2013.01); *A61B 2017/00544* (2013.01); *A61B 2017/00734* (2013.01); *A61B 2017/00911* (2013.01); *A61B 2017/22075* (2013.01); *A61B 2090/374* (2016.02); *A61B 2090/3954* (2016.02); *A61M 25/0113* (2013.01); *A61M 2025/0175* (2013.01)

(58) Field of Classification Search
   CPC ...... A61B 17/0469; A61B 2017/00398; A61B 2017/00539; A61B 2017/00734; A61B 2017/22075; A61B 2017/3409; A61B 2017/00544; A61B 2017/00292; A61B 2090/0811; A61B 2090/374; A61B 2090/3954; A61B 2090/3983; A61B 10/0283; A61B 10/0275; A61B 2010/0208; A61B 34/30; A61B 34/37; A61B 34/70; A61B 34/72; A61M 2025/0004; A61M 2025/0175; A61M 25/0113
   USPC ........ 227/107, 19, 175.1, 110, 111; 600/568, 600/410, 411, 415, 416; 604/117, 156, 604/95.04; 606/119, 130, 170, 171
   See application file for complete search history.

(56) References Cited

U.S. PATENT DOCUMENTS

| | | | | |
|---|---|---|---|---|
| 6,080,181 | A * | 6/2000 | Jensen | B25J 9/1065 606/130 |
| 6,119,973 | A * | 9/2000 | Galloway | B65H 54/2812 242/483.7 |
| 6,402,701 | B1 * | 6/2002 | Kaplan | A61B 10/0233 600/567 |
| 7,090,683 | B2 * | 8/2006 | Brock | A61B 17/0469 606/1 |
| 7,611,474 | B2 * | 11/2009 | Hibner | A61B 10/0266 600/564 |
| 8,038,627 | B2 * | 10/2011 | Hibner | A61B 10/0275 600/568 |
| 8,190,238 | B2 * | 5/2012 | Moll | A61B 1/00039 600/117 |
| 8,235,913 | B2 * | 8/2012 | Hibner | A61B 10/0275 600/568 |
| 8,663,264 | B2 * | 3/2014 | Cesarini | A61B 17/32002 600/566 |
| 8,784,435 | B2 * | 7/2014 | Cooper | A61B 17/3423 606/130 |
| 8,800,838 | B2 * | 8/2014 | Shelton, IV | A61B 17/115 227/175.1 |
| 8,834,488 | B2 * | 9/2014 | Farritor | A61B 1/00158 606/130 |
| 8,951,274 | B2 * | 2/2015 | Adams | A61B 1/303 606/171 |
| 9,028,494 | B2 * | 5/2015 | Shelton, IV | A61B 34/30 606/51 |
| 9,492,234 | B2 * | 11/2016 | Comber | A61B 34/30 |
| 9,827,003 | B2 * | 11/2017 | Ilizaliturri-Sanchez | A61B 17/32002 |
| 2003/0083684 | A1 * | 5/2003 | Cesarini | A61B 17/32002 606/170 |
| 2003/0199787 | A1 * | 10/2003 | Schwindt | A61M 1/0058 600/568 |
| 2004/0092980 | A1 * | 5/2004 | Cesarini | A61B 17/32002 606/159 |
| 2006/0184063 | A1 * | 8/2006 | Miller | A61B 10/0266 600/568 |
| 2007/0060879 | A1 * | 3/2007 | Weitzner | A61B 17/12045 604/95.04 |
| 2007/0167736 | A1 * | 7/2007 | Dietz | A61B 10/0275 600/411 |

OTHER PUBLICATIONS

Wilson, J. F., et al., "Linear Analysis of Uniformly Stressed, Orthotropic Cylindrical Shells," Journal of Applied Mechanics, vol. 53, pp. 249-256, Jun. 1986.

Orgil, G., et al., "Finite Deformations of Nonlinear, Orthotropic Cylindrical Shells," Journal of Applied Mechanics, vol. 53, pp. 257-265, Jun. 1986.

McDonald, G., et al., "Analysis and Performance of a Pneumatic Stepper Motor for Use in MRI Environments," A Robotics Engineering MQP, Worcester Polytechnic Institute, Dec. 5, 2011.

Slightam, J.E., et al., "Novel Integrated Fluid-Power Actuators for Functional End-Use Components and Systems via Selective Laser Sintering Nylon 12," Rapid Prtotyping Research, Milwaukee School of Engineering, pp. 197-211, Aug. 18, 2012.

Miron, G., et al., "Design and Manufactering of Embedded Air-Muscles for a Magnetic Resonance Imaging Compatible Prostate Cancer Binary Manipulator," Journal of Mechanical Design, vol. 135, pp. 011003-10, Jan. 2013.

Slightham, J.E., "Modeling and Stimulation of Biologically Inspired 3D-Printed Fluid-Power Robotic System Architectures," Milwaukee School of Engineering, pp. 1-120, Dec. 2014.

Wilson, J.F., "Bellows-type Springs for Robotics," pp. 109-119.

* cited by examiner

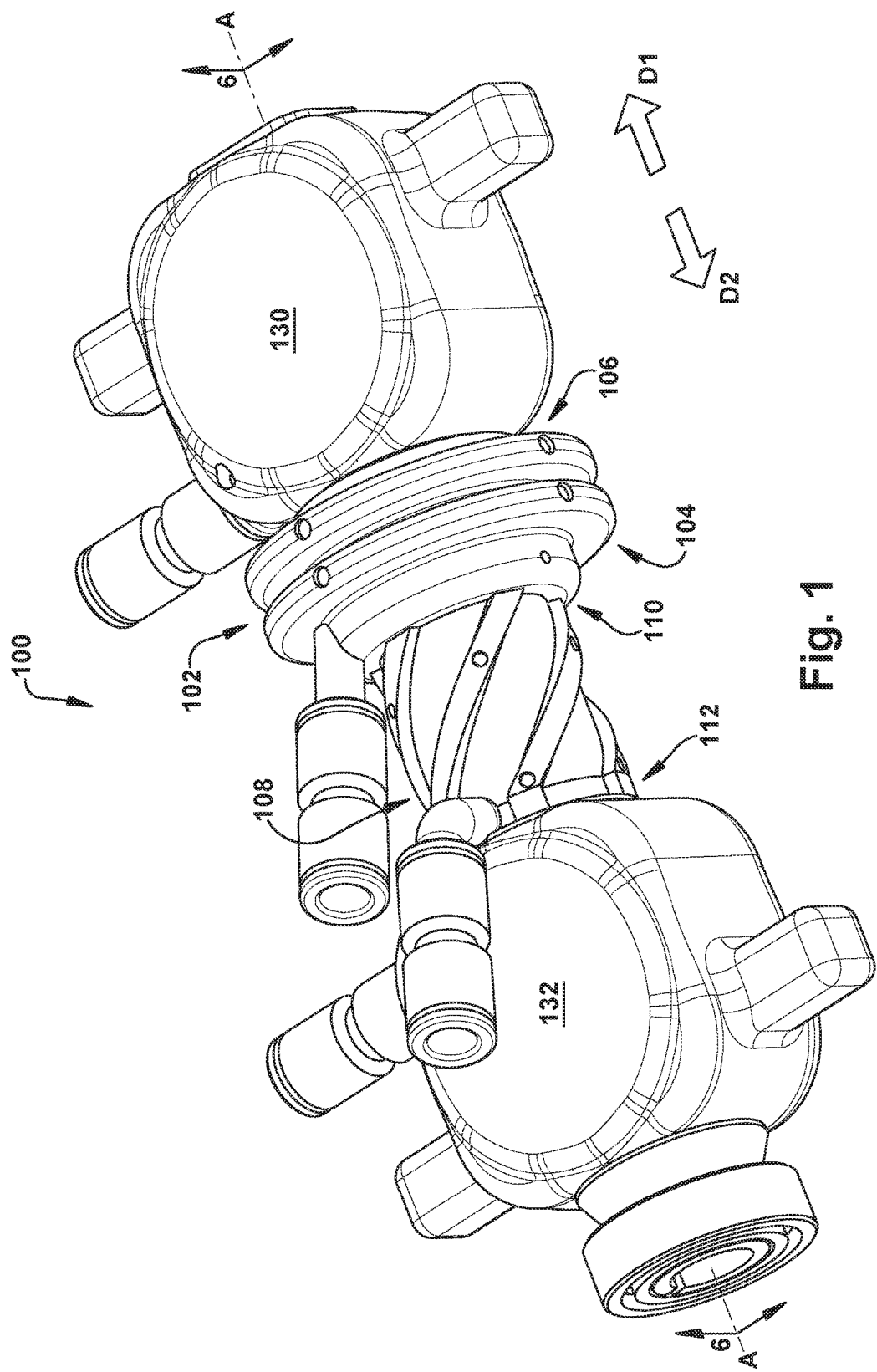

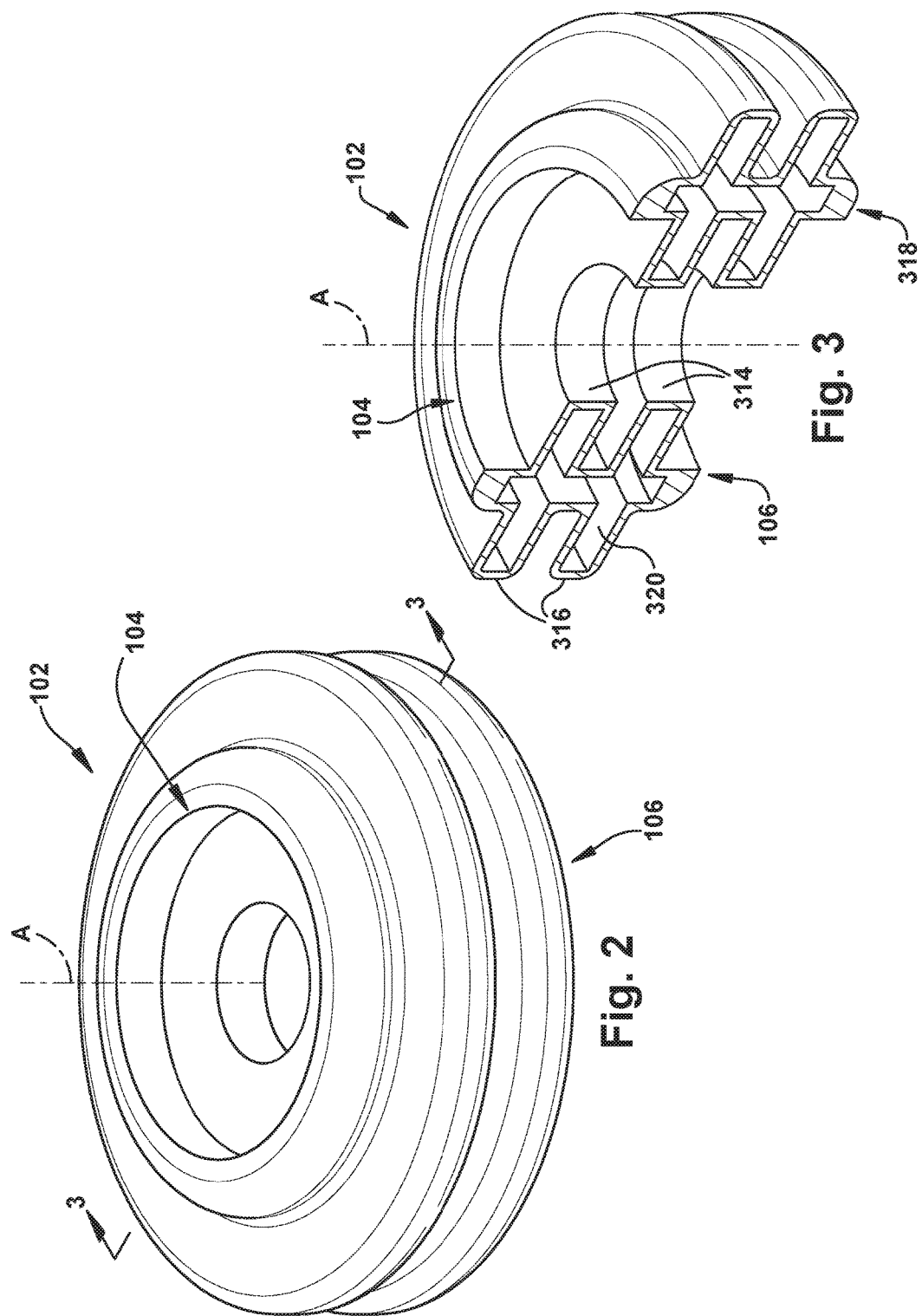

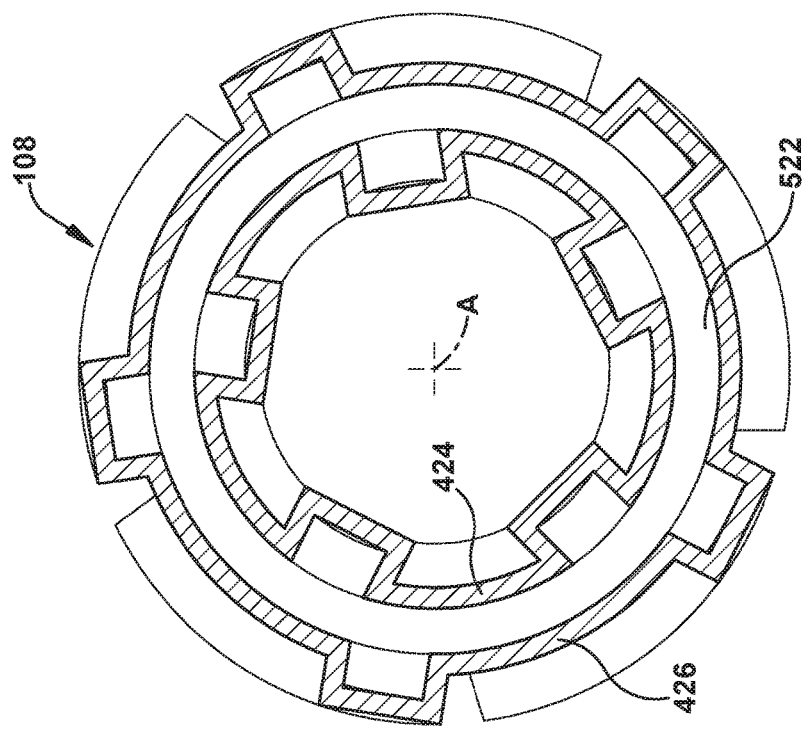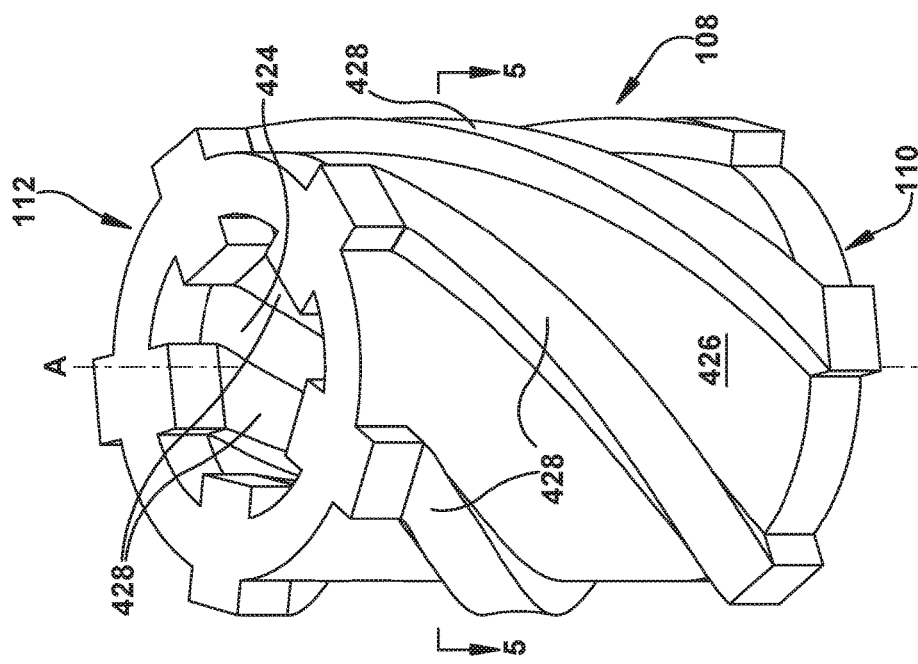

APPARATUS AND METHOD FOR MOVING AN ELONGATE ROD

RELATED APPLICATION

This application claims priority from U.S. Provisional Application No. 62/200,712, filed 4 Aug. 2015, the subject matter of which is incorporated herein by reference in its entirety.

GOVERNMENT SUPPORT

This invention was made with government support under Grant No. EEC-0540834 awarded by The National Science Foundation. The government has certain rights in the invention.

TECHNICAL FIELD

This disclosure relates to an apparatus and method for moving an elongate rod and, more particularly, to a method and apparatus for moving an elongate rod relative to a ground surface longitudinally in at least one of a first direction and a second direction, substantially opposite the first direction, and rotationally in at least one of a clockwise and a counterclockwise direction about a longitudinal axis defined by the elongate rod.

BACKGROUND

Medical robotic systems for image-guided interventions require sterilizable precision actuators. Imaging modalities like computed tomography ("CT") and magnetic resonance ("MR") imaging impose further limitations on actuator design. It is desirable for the robot and its actuators to be transparent to the imager and to not produce artifacts, noise or distortion in the images. Thus, actuator design is restricted to materials and principles of operation that are compatible with the imaging environment. Together with the requirements for sterilizability and precision control, these restrictions present a challenging design problem.

Over the past 20 years, numerous custom MR-compatible actuators and robots have been reported in the literature. Due to the high strength magnetic field of the MR imager, these actuators cannot contain ferromagnetic materials. Pneumatic actuation has been commonly employed because the working principle does not rely on electromagnetism. Thus, these actuators can be constructed solely from dielectric materials.

Other forms of actuation, in particular piezoelectrics, have been employed in a variety of anatomy-specific MR-compatible robots, including several for neurosurgical procedures. While piezoelectrics offer precise and non-backdrivable actuation, many researchers have reported that the high voltage ultrasonic drivers substantially reduce the signal-to-noise (SNR) ratio of the MR imager, precluding the ability to servo the robot motors while simultaneously acquiring images.

Although piezoelectric actuators can be a viable solution for MR-compatible robots, a low-cost yet customizable actuator that does not require extreme care in the design and shielding of drive electronics is desirable. Furthermore, both pneumatic and piezoelectric robots for MRI-guided interventions as reported in the literature have been limited to linear needle trajectories.

SUMMARY

In an aspect, an apparatus for moving an elongate rod relative to a ground surface longitudinally in at least one of a first direction and a second direction, substantially opposite the first direction, and rotationally in at least one of a clockwise and a counterclockwise direction about a longitudinal axis defined by the elongate rod is described. An at least partially longitudinally expandable translation member has a first translation member end held relatively stationary with respect to the ground surface and a second translation member end, longitudinally spaced from the first translation member end. The second translation member end is selectively movable longitudinally with respect to the ground surface via actuation of the translation member. An at least partially helically twistable rotation member has a first rotation member end held relatively stationary with respect to the ground surface and a second rotation member end, longitudinally spaced from the first rotation member end. The second rotation member end is selectively rotatable with respect to the ground surface via actuation of the rotation member. A first locking mechanism is selectively movable longitudinally with respect to the ground surface when urged by the second translation member end. The first locking mechanism is configured to selectively grasp at least a portion of the rod. A second locking mechanism, separate from the first locking mechanism, is selectively movable rotationally about the longitudinal axis with respect to the ground surface when urged by the second rotation member end. The second locking mechanism is configured to selectively grasp at least a portion of the rod. The translation member is actuated to move the second translation member end longitudinally in a chosen one of the first and second directions, which in turn moves the first locking mechanism longitudinally in the chosen one of the first and second directions. The first locking mechanism grasps and releases at least a portion of the rod in coordination with motion of the second translation member end in a chosen one of the first and second directions to move the rod with respect to the ground surface in the chosen one of the first and second directions. The rotation member is actuated to move the second rotation member end rotationally in a chosen one of the clockwise and counterclockwise directions. The second locking mechanism moves rotationally responsive to rotation of the second rotation member end in the chosen one of the clockwise and counterclockwise directions. The second locking mechanism grasps and releases at least a portion of the rod in coordination with motion of the second rotation member end in the chosen one of the clockwise and counterclockwise directions to move the rod with respect to the ground surface as desired in the chosen one of the clockwise and counterclockwise directions.

In an aspect, a method of moving an elongate rod relative to a ground surface longitudinally in at least one of a first direction and a second direction, substantially opposite the first direction, and rotationally in at least one of a clockwise and a counterclockwise direction about a longitudinal axis of the elongate rod is described. A translation member having longitudinally spaced first and second translation member ends is provided. The first translation member end is held stationary. The second translation member end is permitted to selectively move longitudinally relative to the first translation member end. A first locking mechanism configured for selective longitudinal movement under influence of the second translation member end is provided. At least a portion of the rod is selectively grasped with the first locking mechanism. The translation member is actuated with a translational fluid-control valve to move the second translation member end longitudinally in a chosen one of the first and second directions. With the actuated translation member, the first locking mechanism is moved longitudinally in the chosen one of the first and second directions. With the first locking mechanism, at least a portion of the rod is grasped and released in coordination with motion of the first locking mechanism in the chosen one of the first and second directions to move the rod with respect to the ground surface in the chosen one of the first and second directions. A rotation member having longitudinally spaced first and second rotation member ends is provided. The first rotation member end is held stationary. The second rotation member end is permitted to selectively rotate relative to the first rotation member end. A second locking mechanism configured for selective rotational movement under influence of the second rotation member end is provided. At least a portion of the rod is selectively grasped with the second locking mechanism. The rotation member is actuated with a rotational fluid-control valve to move the second rotation member end rotationally in a chosen one of the clockwise and counterclockwise directions. With the actuated rotation member, the second locking mechanism is moved rotationally in the chosen one of the clockwise and counterclockwise directions. With the second locking mechanism, at least a portion of the rod is grasped and released in coordination with motion of the second locking mechanism in the chosen one of the clockwise and counterclockwise directions to move the rod with respect to the ground surface in the chosen one of the clockwise and counterclockwise directions. A binary on/off actuation of the translational fluid control valve is selectively controlled to provide full-step translation control. A binary on/off actuation of the rotational fluid control valve is selectively controlled to provide full-step rotation control. A valve orifice size of the translational fluid control valve is selectively controlled to provide sub-step translation control. A valve orifice size of the rotational fluid control valve is selectively controlled to provide sub-step rotation control.

In an aspect, an apparatus for moving an elongate rod relative to a ground surface longitudinally in at least one of a first direction and a second direction, substantially opposite the first direction, and rotationally in at least one of a clockwise and a counterclockwise direction about a longitudinal axis of the elongate rod is described. An at least partially longitudinally movable translation member has a first translation member end held relatively stationary and a longitudinally spaced second translation member end which is selectively movable longitudinally with respect to the first translation member end via actuation of the translation member. The second translation member end is operatively connected to selectively impart longitudinal motion to the elongate rod. An at least partially helically twistable rotation member has a first rotation member end held relatively stationary and a longitudinally spaced second rotation member end which is selectively rotatable with respect to the first rotation member end via actuation of the rotation member. The second rotation member end is operatively connected to selectively impart rotational motion to the elongate rod. The translation member and the rotation member are integrally joined as a single structure at the time the elongate rod is moved.

In an aspect, a method of moving an elongate rod relative to a ground surface longitudinally in at least one of a first direction and a second direction, substantially opposite the first direction, and rotationally in at least one of a clockwise and a counterclockwise direction about a longitudinal axis of the elongate rod is described. A translation member having longitudinally spaced first and second translation member ends is provided. The first translation member end is held stationary. The second translation member end is permitted to selectively move longitudinally relative to the first translation member end. The translation member is actuated to move the second translation member end longitudinally in a chosen one of the first and second directions. Longitudinal motion is selectively imparted to the elongate rod via operative connection with the second translation member end. A rotation member having longitudinally spaced first and second rotation member ends is provided. The first rotation member end is held stationary. The second rotation member end is permitted to selectively rotate relative to the first rotation member end. The rotation member is actuated to move the second rotation member end rotationally in a chosen one of the clockwise and counterclockwise directions. Rotational motion to the elongate rod is selectively imparted via operative connection with the second rotation member end.

BRIEF DESCRIPTION OF THE DRAWINGS

For a better understanding, reference may be made to the accompanying drawings, in which:

FIG. 1 is a schematic perspective top view of one aspect of the invention;

FIG. 2 is a schematic perspective front view of a component of the aspect of FIG. 1;

FIG. 3 is a partial cross-sectional view of the aspect of FIG. 1;

FIG. 4 is a schematic perspective side view of a component of the aspect of FIG. 1;

FIG. 5 is a cross-sectional view taken along line 5-5 of FIG. 4;

DESCRIPTION OF ASPECTS OF THE DISCLOSURE

Figure 6:
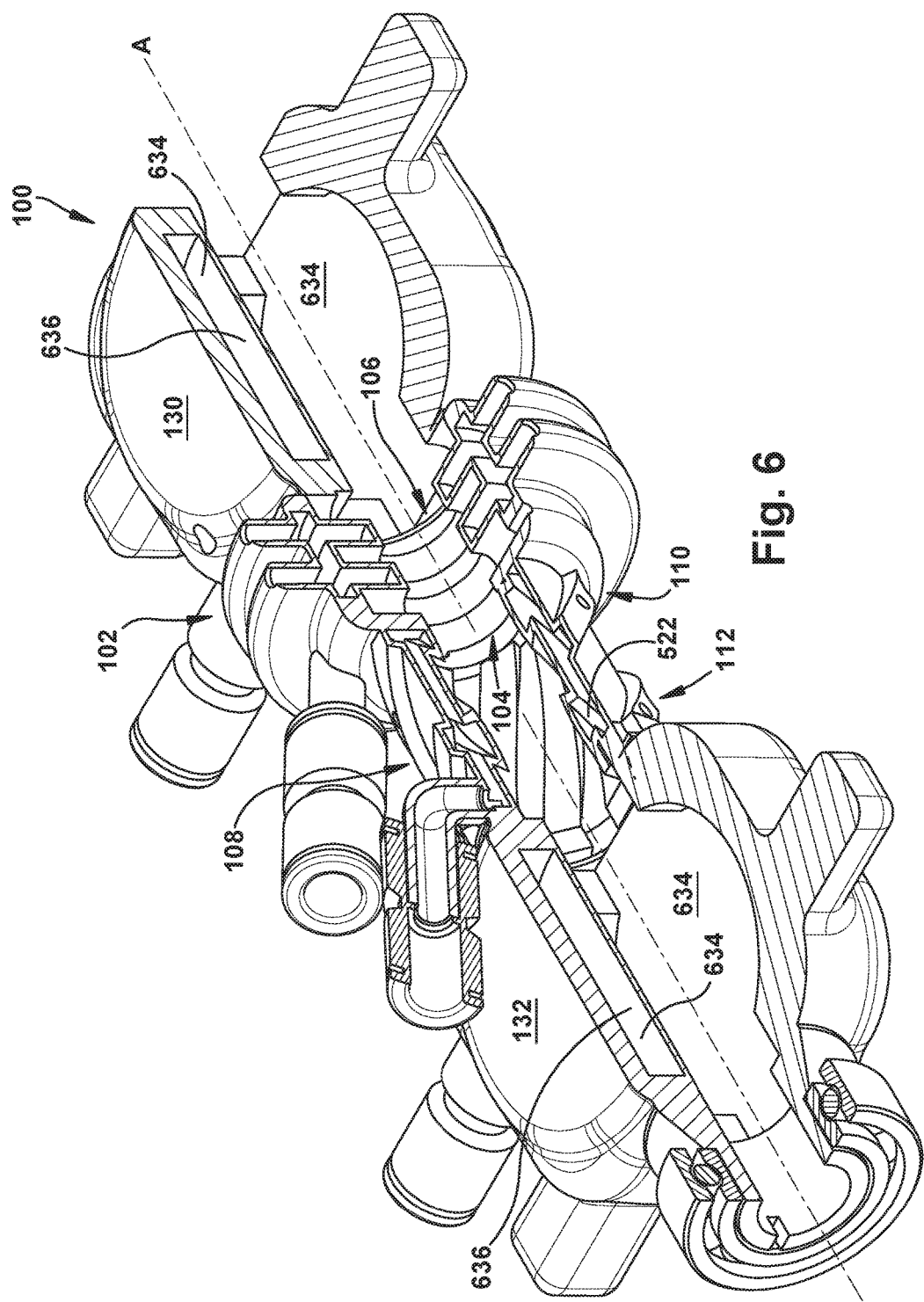
FIG. 6 is a cross-sectional view taken along line 6-6 of FIG. 1.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper", "in front of", "behind", and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

FIG. 1 depicts an apparatus 100 for moving an elongate rod relative to a ground surface longitudinally in at least one of a first direction and a second direction, substantially opposite the first direction. The first and second directions are shown as D1 and D2, respectively, in FIG. 1. The apparatus 100 also can move the elongate rod rotationally in at least one of a clockwise and a counterclockwise direction about a longitudinal axis defined by the elongate rod. Though the elongate rod is absent from FIG. 1, the longitudinal axis is shown at A, in that Figure. The first and second directions D1 and D2 are each substantially parallel to the longitudinal axis A, as shown and described herein.

The apparatus 100 includes an at least partially longitudinally expandable translation member 102 having a first translation member end 104 held relatively stationary with respect to the ground surface and a second translation member end 106, longitudinally spaced from the first translation member end 104. The second translation member end 106 is selectively movable longitudinally with respect to the ground surface via actuation of the translation member 102.

The apparatus 100 also includes an at least partially helically twistable rotation member 108 having a first rotation member end 110 held relatively stationary with respect to the ground surface and a second rotation member end 112, longitudinally spaced from the first rotation member end 110. The second rotation member end 112 is selectively rotatable with respect to the ground surface via actuation of the rotation member 108.

FIGS. 2 and 3 illustrate the translation member 102 in isolation. The translation member 102 shown and described herein is a toroidal bellows, having laterally extending inner and outer bellows 314 and 316, respectively, connected by a substantially cylindrical center spine 318. The "lateral" direction, as used herein, is a direction substantially perpendicular to the longitudinal axis A. The toroidal bellows of the translation member 102 defines a member internal volume 320, which is configured for inflation or deflation under the influence of a provided fluid. As described below, this fluid control of the member internal volume 320 facilitates relative translational or longitudinal motion of the first translation member end 104 and the second translation member end 106, such that the total length of the translation member 102, measured along longitudinal axis A, may be variably controlled.

FIGS. 4-6 illustrate the rotation member 108 in isolation. The rotation member 108 shown and described herein is a helical bellows, that is, a pressurized tube with helical corrugations. Like the translation member 102, the rotation member 108 includes a member internal volume 522. This member internal volume 522 is enclosed by internal and external walls 424 and 426, respectively, extending longitudinally between the first and second rotation member ends 110 and 112. The internal and external walls 424 and 426 each include at least one helical ridge 428. The helical bellows is configured, as described below, so that inflation or deflation of the member internal volume 522 under the influence of a provided fluid facilitates relative rotational motion of the first rotation member end 110 and the second rotation member end 112, such that the rotational position of the second rotation member end 112 relative to the first rotation member end 110, measured radially with respect to longitudinal axis A, may be variably controlled. For many use environments of the present invention, the rotation member 108 may provide almost entirely rotational motion to the rod 846, without any substantial or significant degree of extension/contraction (i.e., longitudinal motion), because the helices on the internal and external walls 424 and 426 are wound in opposite directions.

Returning to FIG. 1, a first locking mechanism 130 may be provided. The first locking mechanism 130 is selectively movable longitudinally with respect to the ground surface when urged by the second translation member end 104. The first locking mechanism 130 is configured to selectively grasp at least a portion of the rod. A second locking mechanism 132, separate from the first locking mechanism 130, may be provided. When present, the second locking mechanism 132 may be selectively movable rotationally about the longitudinal axis A with respect to the ground surface when urged by the second rotation member end 112. The second locking mechanism 132 is configured to selectively grasp at least a portion of the rod.

In use of the apparatus 100, the translation member 102 may be actuated to move the second translation member end 106 longitudinally in a chosen one of the first and second directions D1 and D2, which in turn moves the first locking mechanism 130 longitudinally in the chosen one of the first and second directions D1 and D2. (The term "actuate" is used herein to indicate that an "actuated" structure is being energized, deenergized, charged, discharged, or otherwise put into mechanical action or motion in order to carry out the described function.) As will be described below, the first locking mechanism 130 may grasp and release at least a portion of the rod in coordination with motion of the second translation member end 106 in a chosen one of the first and second directions D1 and D2 to move the rod with respect to the ground surface in the chosen one of the first and second directions.

Similarly, the rotation member 108 may be actuated to move the second rotation member end 112 rotationally in a chosen one of the clockwise and counterclockwise directions. (It should be noted that clockwise and counterclockwise are considered, for the purpose of this description, to be taken about longitudinal axis A by an observer looking in the first direction D1.) The second locking mechanism 132 moves rotationally responsive to rotation of the second rotation member end 112 in the chosen one of the clockwise and counterclockwise directions. Also as will be described below, the second locking mechanism 132 may grasp and release at least a portion of the rod in coordination with motion of the second rotation member end 112 in the chosen one of the clockwise and counterclockwise directions to move the rod with respect to the ground surface as desired in the chosen one of the clockwise and counterclockwise directions.

The rod may therefore be moved longitudinally through action of the translation member 102, and rotationally through action of the rotation member 108. The translation member 102 and the rotation member 108 may be actuated substantially simultaneously for concurrent longitudinal and rotational movement of the elongate rod. Alternatively, the translation member 102 and the rotation member 108 may be actuated at different and separate times for sequential longitudinal and rotational movement of the elongate rod. One of ordinary skill in the art will be able to design a fluid control system, as well as appropriate supporting structures and systems, to carry out any desired serial and/or parallel actuation of the described translation and rotation members 102 and 108, for a particular use environment.

The translation member 102 and the rotation member 108 may be integrally formed in a single piece as a unitary, monolithic structure. The term "unitary" is used herein to indicate that the translation member 102 and the rotation member 108 may collectively form an undivided, whole, single-piece structure at the time of use. It should be understood that a "unitary" structure may be made up of multiple subassemblies, but that these subassemblies are agglomerated together into a single monolithic mass during the manufacturing process. Mere assembly of parts into a final product will not confer "unitary" status to a structure—a "unitary" structure here is one which has parts permanently bonded into a whole, with no substitution of parts contemplated during, or to facilitate, use. For example, the translation member 102 and the rotation member 108, along with any other desired structures of the apparatus 100, may be formed using additive manufacturing techniques. The apparatus 100, and structures thereof, may be formed in any desired manner and using any desired materials. However, for magnetic resonance imaging use applications of the apparatus 100, it is contemplated that non-ferromagnetic materials, such as, but not limited to, plastics and glasses, will be used for most structures.

As previously mentioned, the translation member 102 and the rotation member 108 both define member internal volumes 320 and 522, respectively. The member internal volumes 320 and 522 of the translation member 102 and the rotation member 108 are mutually fluidically separated. Fluid, such as, but not limited to, gas (pneumatic) and liquid (hydraulic) fluids, is selectively provided to, and removed from, each member internal volume 320 and 522 to selectively control fluid pressure in the member internal volumes 320 and 522. Changes in fluid pressure in a corresponding member internal volume 320 and 522 cause both actuation of the translation member 102 to move the second translation member end 106 longitudinally in the chosen one of the first and second directions D1 and D2, and actuation of the rotation member 108 to move the second rotation member end 112 rotationally in the chosen one of the clockwise and counterclockwise directions.

Stated slightly differently, an at least partially longitudinally movable translation member 102 has a first translation member end 104 held relatively stationary and a longitudinally spaced second translation member end 106 which is selectively movable longitudinally with respect to the first translation member end 104 via actuation of the translation member 102. The second translation member end 106 is operatively connected to selectively impart longitudinal motion to the elongate rod. An at least partially helically twistable rotation member 108 has a first rotation member end 110 held relatively stationary and a longitudinally spaced second rotation member end 112 which is selectively rotatable with respect to the first rotation member end 110 via actuation of the rotation member 108. The second rotation member end 112 is operatively connected to selectively impart rotational motion to the elongate rod. The translation member 102 and the rotation member 108 may be integrally joined as a single structure, as shown in the Figures, at the time the elongate rod is moved.

FIG. 6, a cross sectional view of the apparatus 100 of FIG. 1, depicts the first and second locking mechanisms 130 and 132 in additional detail. As shown in FIG. 6, at least one of the first and second locking mechanisms 130 and 132 may be an "active" locking mechanism, which selectively grasps the rod using movement or action. Each of the first and second locking mechanisms 130 and 132 includes two longitudinally extending diaphragms 634, with the pairs of diaphragms 634 of each locking mechanism being arranged in lateral opposition across the elongate rod. The diaphragms 634 are selectively actuable, in pairs, to grasp the elongate rod laterally therebetween. For example, fluid may be provided to a diaphragm space 636 (optionally, but not necessarily, simultaneously) of each of the first and second locking mechanisms 130 and 132, to "inflate" and push the diaphragms inward toward the longitudinal axis A, thus pinching the elongate rod therebetween. While the diaphragm spaces 636 are only shown in FIG. 6 for the upper diaphragms 634 of each of the first and second locking mechanisms 130 and 132, a similar arrangement is present to actuate the lower diaphragms 634 of those locking mechanisms.

Figure 7:
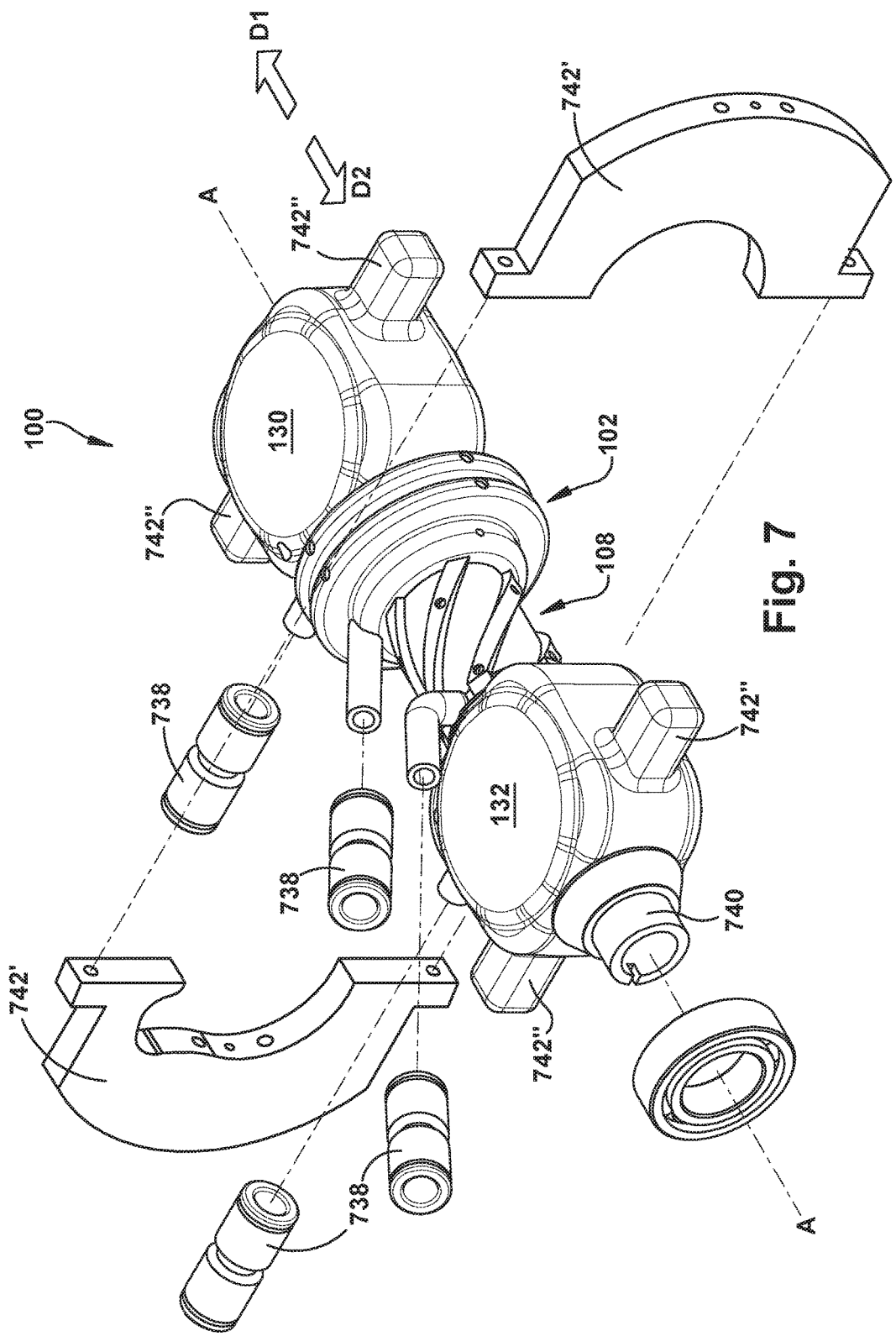
FIG. 7 is an exploded view of the aspect of FIG. 1.

Turning to FIG. 7, an exploded view of the apparatus 100 is shown. Here, fluidic coupling fittings 738 are shown, by which each of the translation member 102, rotation member 108, first locking mechanism 130, and second locking mechanism 132 may be fluidically connected to a source of fluid energy. For example, the apparatus 100, and related structures, could be configured to accept operative fluid from a standard pneumatic source, such as those commonly available in healthcare settings.

FIG. 7 also depicts a "passive" locking mechanism 740, which could be used in addition to, or instead of, the "active" locking mechanisms 130 and 132 previously described. For example, the passive locking mechanism 740 could be a resilient collar, such as a rubberized cylinder, that fits tightly to the elongate rod. 28. The passive locking mechanism 740 is shown in the Figures and is described herein as being a third locking mechanism 740, for clarity, though could be used in the same location as, and/or replace, either or both of the first and second locking mechanisms 130 and 132.

As shown in FIG. 7, the third locking mechanism 740 may be separate from the first locking mechanism 130 and may be longitudinally spaced from the first locking mechanism 130 with the rotation member 102 and translation member 108 interposed therebetween. Regardless of the exact configuration of the apparatus 100, and/or the nature of the third locking mechanism 740 and any "active" locking mechanisms which are also provided to the apparatus 100, though, the "passive" third locking mechanism applies frictional lateral pressure to at least a portion of the rod. The frictional lateral pressure of the third locking mechanism 740 is configured to be of such a magnitude as to permit the rod to move longitudinally under influence of the translation member 102, but to resist longitudinal force of a magnitude less than that applied by the translation member 102. In this manner, the third locking mechanism 740 may work to prevent incidental motion of the rod, such as backsliding, when the rod is not being grasped by the first locking mechanism 130, and/or any second locking mechanism 132 which is provided to the apparatus 100.

FIG. 7 also depicts a plurality of constraining structures 742, with each constraining structure 742 being associated with at least one of the rotation member 102 and the translation member 108. There are two types of constraining structures 742 shown in FIG. 7, though each constraining structure 742, and any other similar structures which may be provided to the apparatus 100, mechanically facilitates the rotational and translational actions of the elongate rod. For example, the constraining structure 742 can locate, guide, separate, direct, or otherwise assist with achieving desired translation and rotation results for the elongate rod with the apparatus 100. A two-piece "bracket" type constraining structure 742' may be used to help support the apparatus 100 with respect to an adjacent housing structure, as will be described below. The two-piece constraining structure 742' may also assist with mechanically separating the rotational and translational actions of the apparatus 100 for separate and sequential rotary and longitudinal action of the rod.

The first and second locking mechanisms 130 and 132 of the apparatus 100 are also shown in FIG. 7 as including tab type constraining structures 742". Because each of the first and second locking mechanisms 130 and 132 is associated with the translation member 102 or the rotation member 108, these tab type constraining structures 742" can interface with slots in an adjacent housing structure to resist unwanted motion and thereby both locate the apparatus 100 within the housing, and channel the motion provided by the apparatus in a desired manner with respect to the elongate rod. In addition to the described constraining structure 742, one or more collars, which might include ball bearings, lubricants, or other friction-reducing features, can be provided to mount the apparatus 100 in a housing structure as desired.

Figure 8:
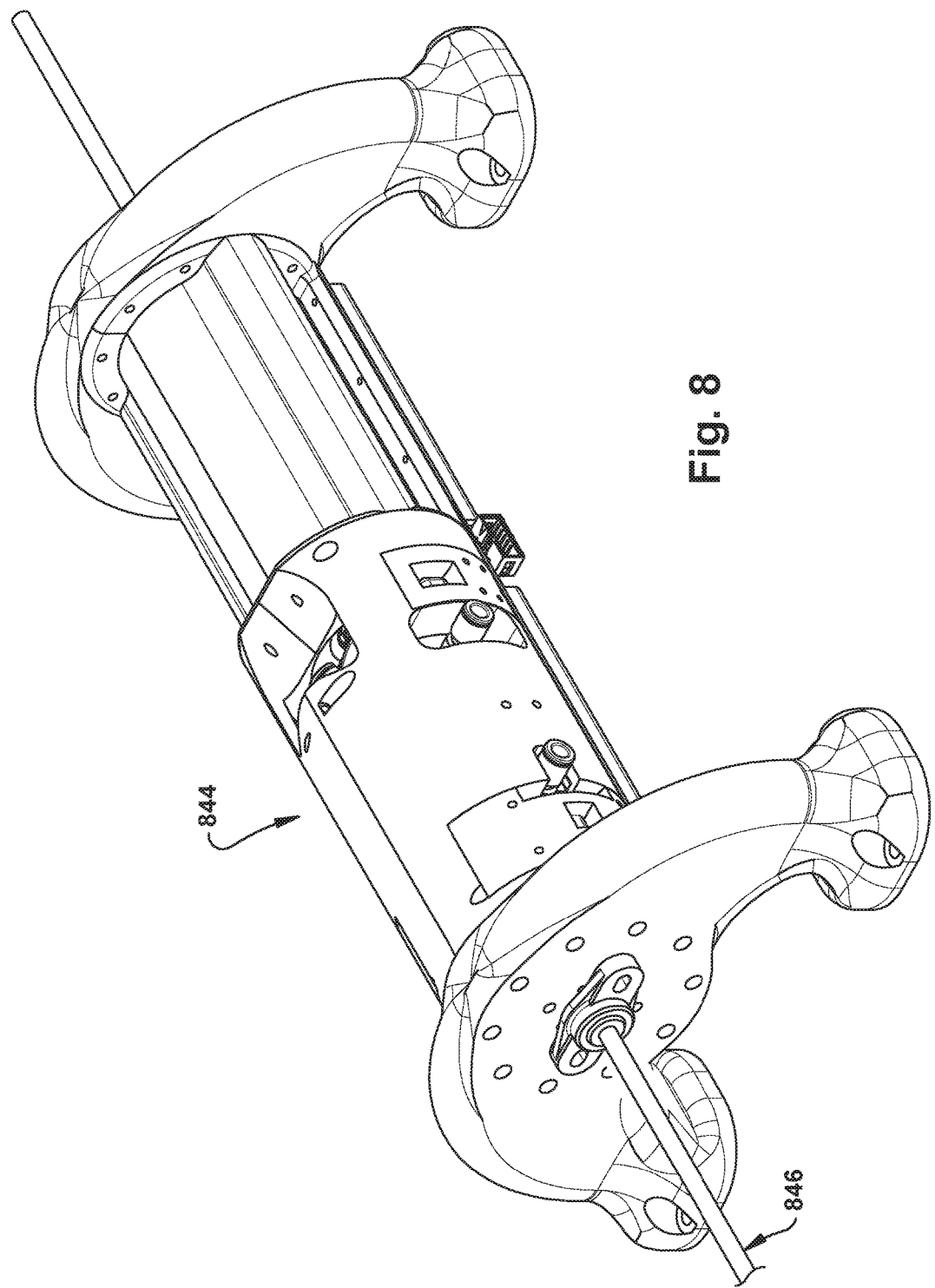
FIG. 8 is a perspective side view of a device including the aspect of FIG. 1.

For example, FIG. 8 depicts a housing 844 which can be used to position, protect, and otherwise facilitate use of the apparatus 100 within a desired use environment. Because the use environment is being described herein as a steerable needle intervention for a subject in an MR imaging environment, the elongate rod 846 is shown as at least a portion of a steerable needle, with the subject-entering end of the needle being toward the left side of the page, in the orientation of FIG. 8. One example steerable needle which could be used with the apparatus 100 is shown and described in U.S. patent application Ser. No. 13/679,512, entitled "Motive Device for Use in Magnetically-Sensitive Environments", filed 16 Nov. 2012 by David B. Comber et. al (now U.S. Pat. No. _____, issued YY/ZZ/AA), the entire contents of which are incorporated herein by reference.

Figure 9:
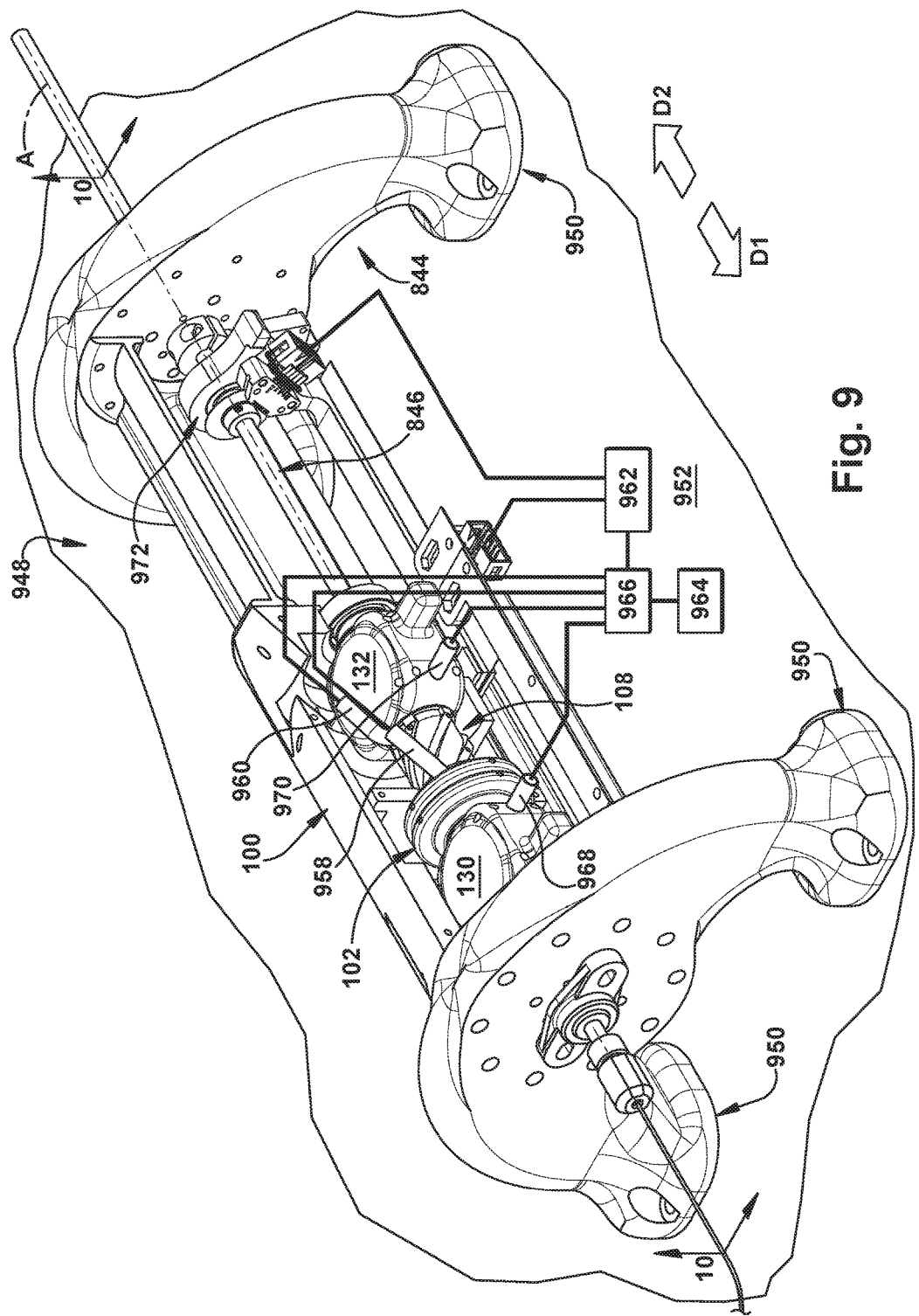
FIG. 9 is a schematic partial side view of the device of FIG. 10.

FIGS. 9-12 depict an interior of the housing 844 which itself collectively forms a device 948 along with the apparatus 100 and a plurality of other structures and elements. In FIG. 9, the arch-shaped cover has been removed from the housing 844 to depict the positioning of the apparatus 100 with respect to other structures inside the housing 844. The rod 846 extends through the housing 844 and defines the longitudinal axis A. The device 948 also includes a plurality of legs 950, which help to support the apparatus 100 in a desired relationship with a ground surface 952, upon which the device 940 rests.

Figure 10:
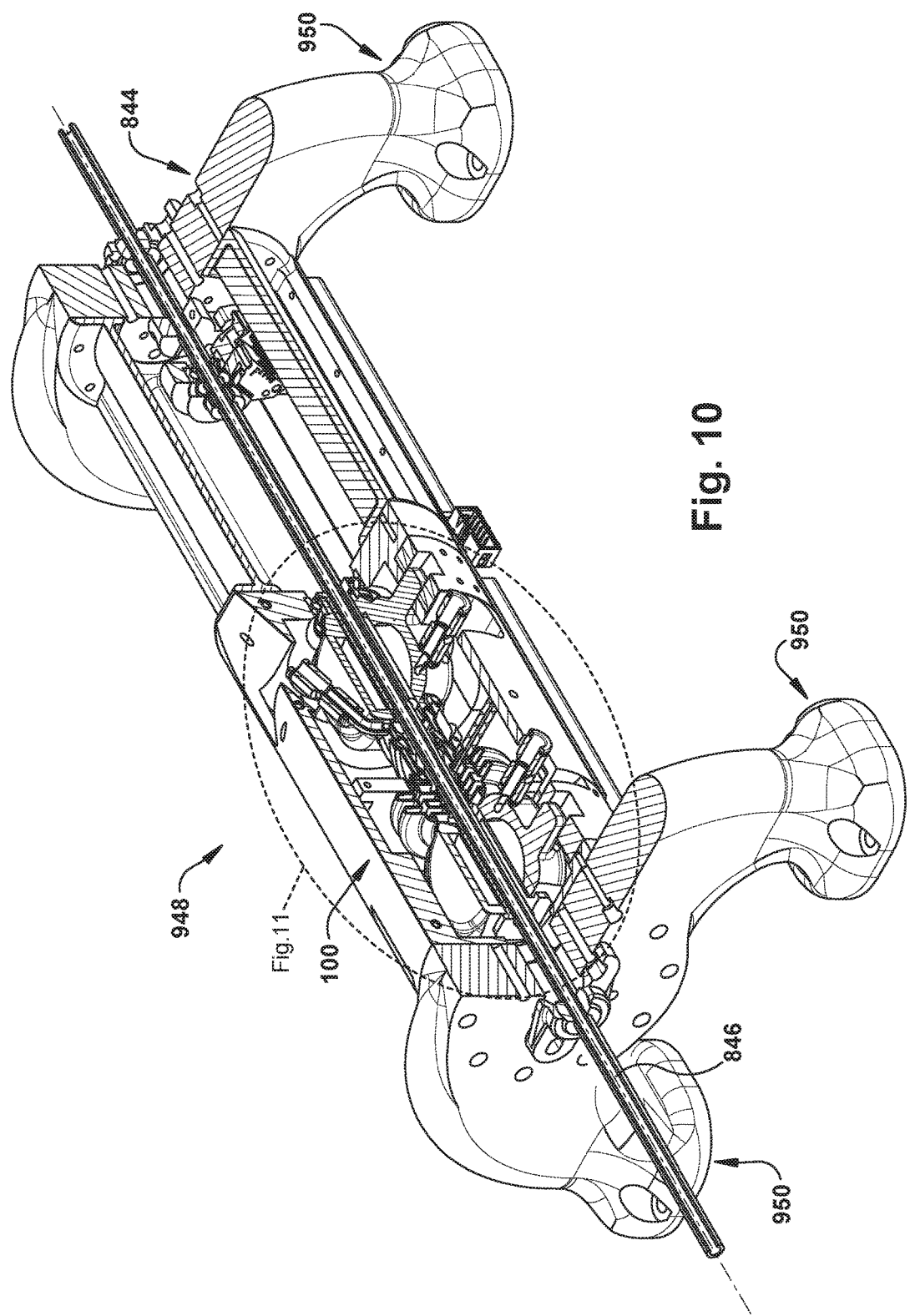
FIG. 10 is a cross-sectional view taken along line 10-10 of FIG. 9.
Figure 11:
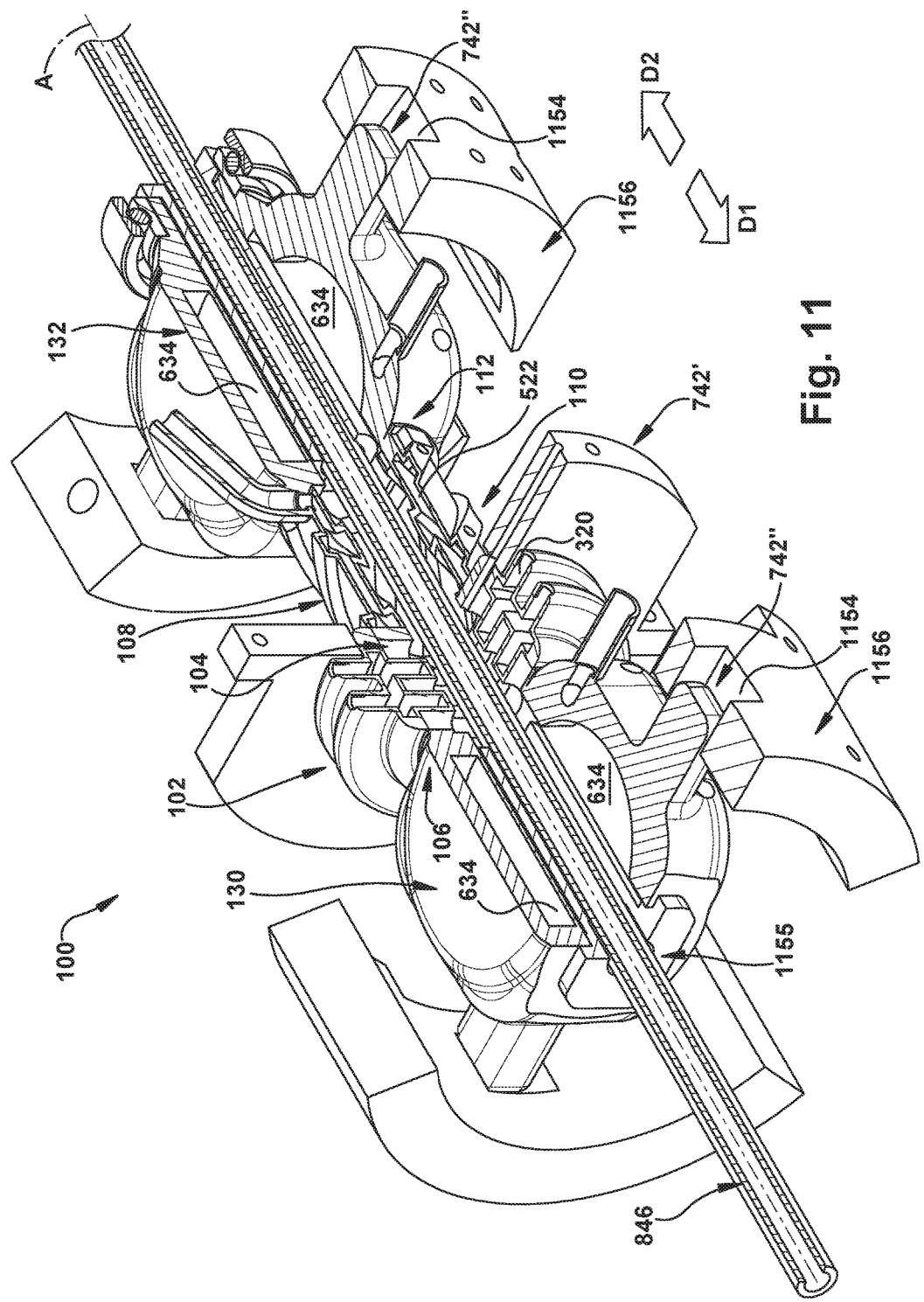
FIG. 11 is a detail view of area "11" of FIG. 10.

FIGS. 10-11 show the apparatus 100 in place within the housing 844. The translation member 102 and the rotation member 108 both define member internal volumes 320 and 522. The member internal volumes 320 and 522 of the translation member 102 and the rotation member 108 are mutually fluidically separated. Fluid is selectively provided to, and removed from, each member internal volume 320 and 522 to selectively control fluid pressure in the member internal volumes 320 and 522. Changes in fluid pressure in a corresponding member internal volume 320 and 522 cause both (1) actuation of the translation member 102 to move the second translation member end 106 longitudinally in the chosen one of the first and second directions D1 and D2 and (2) actuation of the rotation member 108 to move the second rotation member end 112 rotationally in the chosen one of the clockwise and counterclockwise directions.

This motion of the second translation member end 106 and the second rotation member and 112 is accomplishing coordination with selective actuation of the first and second locking mechanisms 130 and 132. For example, the first locking mechanism 130 is selectively movable longitudinally with respect to the ground surface 952 when urged by the second translation member end 106, and the first locking mechanism 130 is configured to selectively grasp at least a portion of the rod 846, to carry the rod 846 along with itself in the first or second direction D1 or D2, as urged by the second translation member end 106. Likewise, the second locking mechanism 132, which is separate from the first locking mechanism 102, is, similarly, selectively movable rotationally about the longitudinal axis A with respect to the ground surface 952 when urged by the second rotation member end 112. The second locking mechanism 132 is configured to selectively grasp at least a portion of the rod 846, to carry the rod 846 along with itself in the clockwise or counterclockwise direction, as urged by the second rotation member end 112.

The constraining structures 742", as shown in at least FIG. 11, may be used in concert with slots 1154 in, or operatively connected to, portions of the housing 844, such as the locking mechanism carriers 1156 shown (which themselves are connected to the housing 844 in a suitable manner, which may include being slidably or pivotably connected, to guide and facilitate the described motion of the first and second locking mechanisms 130 and 132). It is also or instead contemplated that the slots 1154 themselves may be configured to allow some movement of the constraining structures 742" therein, while the locking mechanism carriers 1156 remain stationary with respect to the housing 844.

FIG. 11 also includes a C clamp 1155, which may assist with concentrating the force applied by the diaphragms 634 of the first and second locking mechanisms 130 and 132, to assist with grasping of the rod 846 as desired. Each C clamp 1155 is located between the diaphragms 634 of a selected one of the first and second locking mechanisms 130 and 132 and at least partially encircles the rod 846 to pinch against the rod 846 under the laterally urging force of the diaphragms 634 being actuated.

With reference back to FIG. 9, the apparatus 100 may include a translational fluid-control valve (shown schematically at 958, though optionally located any desired distance from the apparatus 100 itself) for selectively actuating the translation member 102 to move the second translation member end 106 longitudinally in the chosen one of the first and second directions D1 and D2. For example, an increase of fluid pressure in the member internal volume 320 of the translation member 102 to a positive translation fluid pressure, above a resting translation fluid pressure, may cause expansion of the translation member 102 from a resting configuration to an expanded configuration and thus urge movement of the second translation member end 106 in the first direction D1. Analogously, a decrease of fluid pressure in the member internal volume 320 of the translation member 102 below the positive translation fluid pressure— whether back down to, or even below, the resting translation fluid pressure—may cause contraction of the translation member 102 from the expanded configuration and thus urge movement of the second translation member end 106 in the second direction D2.

The apparatus 100 may also include a rotational fluid-control valve (shown schematically at 960, though optionally located any desired distance from the apparatus itself) for selectively actuating the rotation member 108 to move the second rotation member end 112 rotationally in the chosen one of the clockwise and counterclockwise directions. For example, an increase of fluid pressure in the member internal volume 522 of the rotation member 108 to a positive rotation fluid pressure, above a resting rotation fluid pressure, may cause expansion of the rotation member 108 from a resting configuration to an expanded configuration and thus urge movement of the second rotation member end 112 in a selected one of the clockwise and counterclockwise directions. Analogously, a decrease of fluid pressure in the member internal volume 522 of the rotation member 108 from the positive rotation fluid pressure— whether back down to, or even below, the resting rotation fluid pressure—may cause contraction of the rotation member 108 from the expanded configuration and thus urge movement of the second rotation member end 112 in the other one of the clockwise and counterclockwise directions.

As shown schematically in FIG. 9, a controller (shown schematically at 962) may interface with one or more fluid sources (shown schematically at 964) and/or with the translational and rotational fluid control valves 958 and 960, such as through valve controller 966, to provide desired control of fluid to the apparatus 100 for a particular use application of the device 948. For example, the controller 962, or any other desired control mechanism, can selectively control a binary on/off actuation of the translational fluid control valve 958 to provide full-step translation control and can selectively control a binary on/off actuation of the rotational fluid control valve 960 to provide full-step rotation control. Likewise, the controller 962, or any other desired control mechanism, can selectively control a valve orifice size of the translational fluid control valve 958 to provide sub-step translation control and can selectively control a valve orifice size of the rotational fluid control valve 960 to provide sub-step rotation control. In this way, the controller 962 can provide full step rotation and translation control to cause the elongate rod 846 to approach a predetermined desired end position under "coarse" control (e.g., 0.4-0.6 mm translation and 0.4-0.6° rotation). Then, when the rod 846 has fairly quickly approached via full steps relatively near to the predetermined desired end position (such as, for example, within about 1 to 2 steps), the controller 962 can switch to "fine" control (e.g., 0.01-0.10 mm translation and 0.02-0.20° rotation), to more slowly and accurately approach the predetermined desired end position through sub-steps.

The controller 962 (which may control the fluid valves described herein directly, and/or may provide any other desired electronic and/or fluid control to the device 948), the valve controller 966 (when present; which may be provided to assist the controller 962 with specific fluid control tasks), or any other desired control mechanism or scheme can selectively actuate the first locking mechanism 130 (such as with the aid of a first locking mechanism valve, shown schematically at 968 in FIG. 9) to grasp and release the elongate rod 846 in predetermined coordination with expansion and contraction of the translation member 102 to and from the expanded configuration to cause predetermined motion of the elongate rod 846 in at least one of the first and second directions D1 and D2. The controller 962, the valve controller 966, or any other desired control mechanism or scheme can also selectively actuate the second locking mechanism 132 (such as with the aid of a second locking mechanism valve, shown schematically at 970 in FIG. 9) to grasp and release the elongate rod 846 in predetermined coordination with expansion and contraction of the rotation member 108 to and from the expanded configuration to cause predetermined motion of the elongate rod 846 in at least one of the clockwise and counterclockwise directions. It should be noted that the expansion and contraction of the rotation member 108, and the resultant rotational motion which is imparted to the rod 846, will depend upon the design of the rotation member 108, and particularly upon the sign and magnitude of geometrical torsion of the helical ridges 428. One of ordinary skill in the art can provide a suitable rotation member 108 to achieve desired rotation direction and magnitude under particular fluid pressures.

More specifically, in full step control mode of the apparatus 100, the translational and rotational fluid control valves 958 and 960 may be sequenced to advance the rod 846 toward the final desired translational or linear position. Using any desired number and type of control valves (such as, but not limited to, the translational fluid control valve 958, the rotational fluid control valve 960, the first locking mechanism valve 968, and/or the second locking mechanism valve 970), the following sequence may be repeated to advance the rod 846 in the first direction D1:

(1) Actuate first locking mechanism 130.
(2) Deactuate second locking mechanism 132.
(3) Actuate translation member 102.
(4) Actuate second locking mechanism 132.
(5) Deactuate first locking mechanism 130.
(6) Deactuate translation member 102.

To retract the rod 846 in the second direction D2, the material stiffness of the translation member 102 may be used to impart a restoring force. The following sequence may be repeated to achieve negative (here, in the second direction D2) linear displacement or longitudinal travel of the rod 846:

(1) Actuate translation member 102.
(2) Actuate first locking mechanism 130.

(3) Deactuate second locking mechanism 132.
(4) Deactuate translation member 102.
(5) Actuate second locking mechanism 132.
(6) Deactuate first locking mechanism 130.

In the immediately previous two six-step sequences, there is purely longitudinal motion imparted to the rod 846—no rotational motion is present.

In full step control mode of the rotation member 108, the following sequence may be repeated to rotate the tube in the clockwise direction toward the final desired angular displacement:

(1) Actuate second locking mechanism 132.
(2) Deactuate first locking mechanism 130.
(3) Actuate rotation member 108.
(4) Actuate first locking mechanism 130.
(5) Deactuate second locking mechanism 132.
(6) Deactuate rotation member 108.

The rod 846 may be rotated in the opposite direction, such as counterclockwise, optionally with assistance from the internal stiffness of the rotation member 108 to impart a restoring torque. The following sequence may be repeated to achieve reverse (here, in the counterclockwise direction) angular displacement:

(1) Actuate rotation member 108.
(2) Actuate second locking mechanism 132.
(3) Deactuate first locking mechanism 130.
(4) Deactuate rotation member 108.
(5) Actuate first locking mechanism 130.
(6) Deactuate second locking mechanism 132.

In the immediately previous two six-step sequences, there is purely rotational motion imparted to the rod 846—no longitudinal motion is present. However, as previously discussed, these four six-step sequences can be carried out sequentially or at least partially simultaneously to achieve desired translational and rotational motion of the rod 846. The above four apparatus 100 actuation sequences ensure that at least one of the first and second locking mechanisms 130 and 132 is engaging the rod 846 at all times.

When the rod 846 displacement is within one step increment of the desired final displacement, as previously mentioned, the controller 962 may switch modes from full step control to sub-step control. For translational and rotational displacement in sub-step control mode, the first and second locking mechanisms 130 and 132 may engage or grasp the rod 846, and a model-based, sliding mode controller 962 may command fluid flow to the translation and rotation members 102 and 108 using their respective translational and rotational fluid control valves 958 and 960 (proportional spool type).

Figure 12:
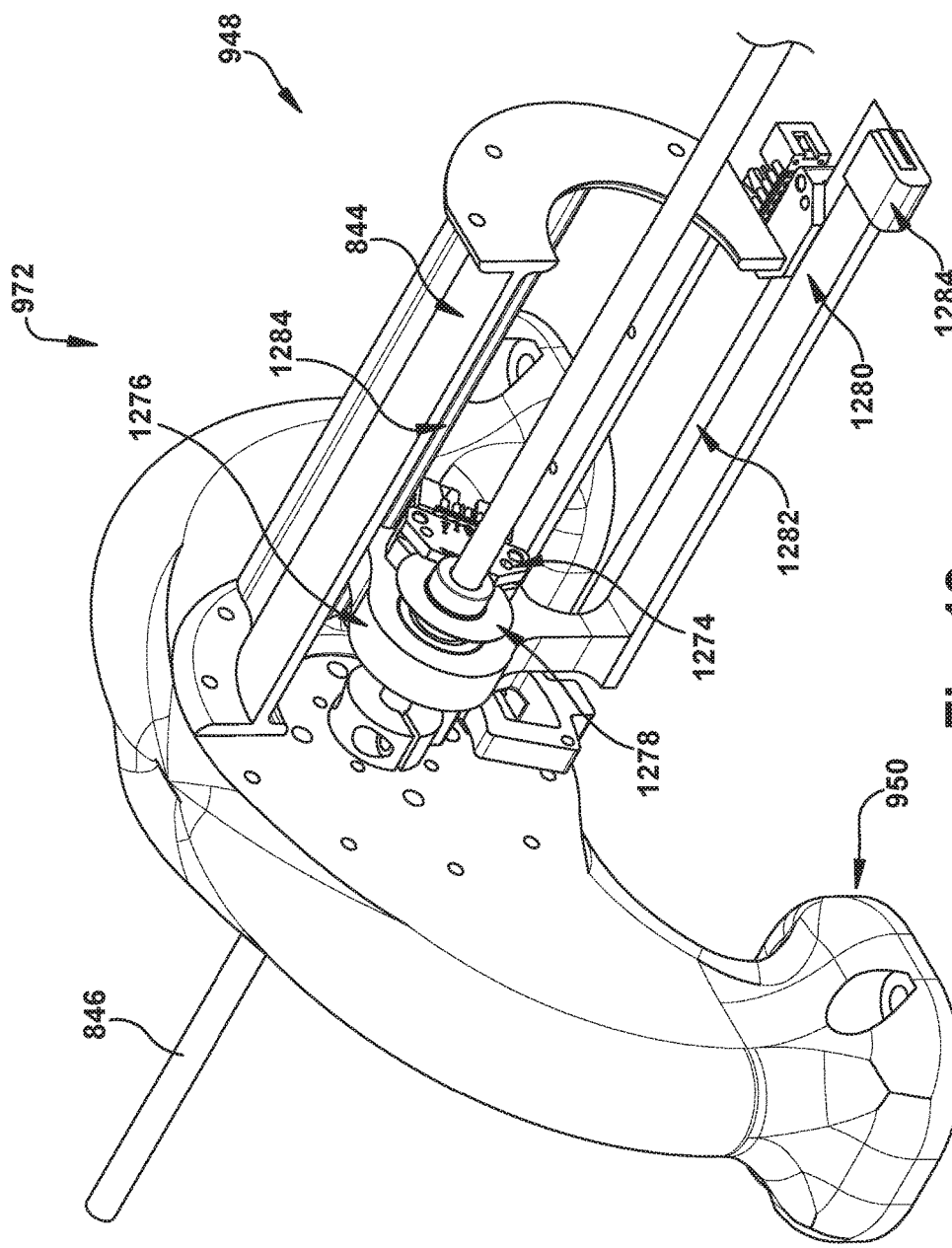
FIG. 12 is a schematic partial side view of the device of FIG. 8.

The relative and absolute rotational and longitudinal positions of the rod 846 can be measured, tracked, and/or controlled in any suitable manner, such as a scheme including the controller 962, which is shown in FIG. 9 as being schematically attached to a sensor mechanism 972. Details of one example suitable sensor mechanism 972 are shown in FIG. 12. In this Figure, a longitudinally opposite end of the device 948 from the actuator 100 is shown, but a sensor mechanism 972, or portions thereof, could be located in any suitable relationship to the apparatus 100. High-resolution, indexed optical encoders may be provided to ensure precision feedback and MR-compatibility. A rotary encoder module 1274 may be affixed to a rotary encoder mount 1276. This rotary encoder module 1274 translates with, but does not rotate with, the rod 846, because it interfaces with the rod 846 via a ball bearing. A transparent code disc 1278 (e.g., one capable of 5000 counts per revolution) may be mounted to, and rotate with, the rod 846. A linear encoder module 1280 may be affixed to the housing 844, while a transparent code strip 1282 (e.g., one having 500 lines per inch) may mounts to the rotary encoder mount 1276 and thereby translate with the rod 846. Two linear guides 1284 may support the rotary encoder mount 1276 and code strip 1282, and may constrain these against angular displacements. For good noise rejection during MRI scanner experiments, a cable driver chip may be mounted to each encoder module 1274 and 1280 to convert the signals from single-ended to differential. One of ordinary skill in the art could readily implement a similar sensor mechanism 972, or any other suitable sensor mechanism 972 to assist with controlling, tracking, recording, sensing, or any other sensing and control actions as desired for a particular use environment.

Figure 13:
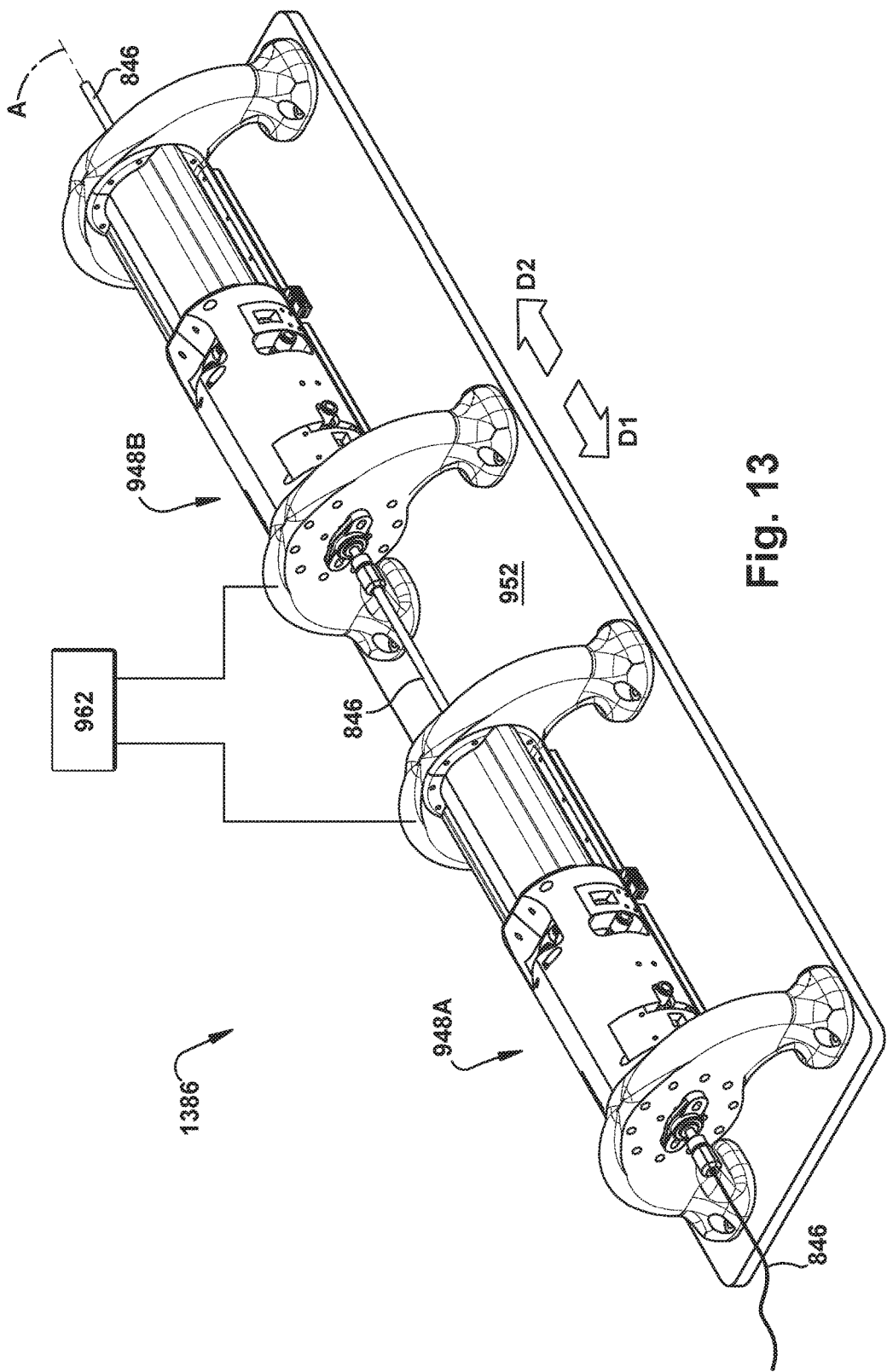
FIG. 13 is a schematic perspective side view of a system including the device of FIG. 8.

FIG. 13 depicts a system 1386 for moving an elongate rod 846 relative to a ground surface 952 longitudinally in at least one of a first direction D1 and a second direction D2, substantially opposite the first direction D1, and rotationally in at least one of a clockwise and a counterclockwise direction about a longitudinal axis of the elongate rod. The system 1386 includes an operatively connected plurality of apparatuses 100, substantially similar to those described above. These apparatuses 100 (two, in this case) are each shown as being associated with different devices 948A and 948B, however, it is contemplated that a plurality of apparatuses 100 could be provided in a single device 948. As shown schematically in FIG. 13, a single controller 962 is operatively connected to both of the devices 948A and 948B, for coordination of longitudinal and rotational motion. However, one of ordinary skill in the art could readily provide any desired number and type of devices 948, and apparatuses 100, to be used serially and/or in parallel for a particular use environment.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. The design of the apparatus 100, and of the device 948 as a whole, may be modular such that larger or smaller step sizes, and the use with different size rods 846, may be available with a single apparatus 100 and/or device 948, through substitution of differently dimensioned components. The apparatus 100 may be hermetically sealed, a desirable quality in surgical environments for sterility reasons: hermetic sealing prevents contaminants such as blood or cerebrospinal fluid from entering the fluid circuit (that is, the control valves, transmission lines, pressure sensors, apparatus 100 components, and reservoirs employed to control the apparatus 100). Particular ones of the first and second translation member ends 104 and 106, and of the first and second rotation member ends 110 and 112, are described and shown herein as being stationary or movable, relative to the ground surface; however, one of ordinary skill in the art could readily anchor or release these ends in a particular use environment to exhibit any desired combination of stationary or movable properties, as desired to achieve particular motion of the apparatus 100 and, thus, of the rod 846 (e.g., one or both of the first translation and rotation member ends 104 and 110 could be permitted to move, while one or both of the second translation and rotation member ends 106 and 112 could be held stationary with respect to the ground surface). It should be noted that, especially for use in MR-sensitive environments, any desired portions of the device 948 such as, but not limited to, fluid supplies, controllers, sensors, valve manifolds, or any other suitable components, could be located remotely—e.g., outside the magnetically sensitive area—but are shown schematically in the Figures as being relatively close to other components of the device 948, for ease of depiction. This description references the apparatus 100 as being actuated fluidically, but it is contemplated that any suitable control and/or energization scheme may be provided, such as, but not limited to, electrical, magnetic, and piezoelectrical. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An apparatus for moving an elongate rod relative to a ground surface longitudinally in at least one of a first direction and a second direction, substantially opposite the first direction, and rotationally in at least one of a clockwise and a counterclockwise direction about a longitudinal axis defined by the elongate rod, the apparatus comprising:

an at least partially longitudinally expandable translation member having a first translation member end held relatively stationary with respect to the ground surface and a second translation member end, longitudinally spaced from the first translation member end, the second translation member end being selectively movable longitudinally with respect to the ground surface via actuation of the translation member;

an at least partially helically twistable rotation member having a first rotation member end held relatively stationary with respect to the ground surface and a second rotation member end, longitudinally spaced from the first rotation member end, the second rotation member end being selectively rotatable with respect to the ground surface via actuation of the rotation member;

a first locking mechanism selectively movable longitudinally with respect to the ground surface when urged by the second translation member end, the first locking mechanism being configured to selectively grasp at least a portion of the rod; and a second locking mechanism, separate from the first locking mechanism, the second locking mechanism being selectively movable rotationally about the longitudinal axis with respect to the ground surface when urged by the second rotation member end, the second locking mechanism being configured to selectively grasp at least a portion of the rod;

wherein the translation member is actuated to move the second translation member end longitudinally in a chosen one of the first and second directions, which in turn moves the first locking mechanism longitudinally in the chosen one of the first and second directions;

wherein the first locking mechanism grasps and releases at least a portion of the rod in coordination with motion of the second translation member end in a chosen one of the first and second directions to move the rod with respect to the ground surface in the chosen one of the first and second directions;

wherein the rotation member is actuated to move the second rotation member end rotationally in a chosen one of the clockwise and counterclockwise directions, the second locking mechanism moving rotationally responsive to rotation of the second rotation member end in the chosen one of the clockwise and counterclockwise directions; and wherein the second locking mechanism grasps and releases at least a portion of the rod in coordination with motion of the second rotation member end in the chosen one of the clockwise and counterclockwise directions to move the rod with respect to the ground surface as desired in the chosen one of the clockwise and counterclockwise directions.

2. The apparatus of claim 1, wherein the translation member and the rotation member are integrally formed in a single piece as a monolithic structure.

3. The apparatus of claim 2, wherein the translation member and the rotation member are formed using additive manufacturing techniques.

4. The apparatus of claim 1, wherein the translation member and the rotation member both define member internal volumes, the member internal volumes of the translation member and the rotation member being mutually fluidically separated, and wherein fluid is selectively provided to, and removed from, each member internal volume to selectively control fluid pressure in the member internal volumes, wherein changes in fluid pressure in a corresponding member internal volume cause both actuation of the translation member to move the second translation member end longitudinally in the chosen one of the first and second directions, and actuation of the rotation member to move the second rotation member end rotationally in the chosen one of the clockwise and counterclockwise directions.

5. The apparatus of claim 4, including a translational fluid-control valve for selectively actuating the translation member to move the second translation member end longitudinally in the chosen one of the first and second directions.

6. The apparatus of claim 4, wherein an increase of fluid pressure in the member internal volume of the translation member to a positive translation fluid pressure, above a resting translation fluid pressure, causes expansion of the translation member from a resting configuration to an expanded configuration and movement of the second translation member end in the first direction, and wherein a decrease of fluid pressure in the member internal volume of the translation member below the positive translation fluid pressure causes contraction of the translation member from the expanded configuration and movement of the second translation member end in the second direction.

7. The apparatus of claim 6, including a controller selectively actuating the first locking mechanism to grasp and release the elongate rod in predetermined coordination with expansion and contraction of the translation member to and from the expanded configuration to cause predetermined motion of the elongate rod in at least one of the first and second directions.

8. The apparatus of claim 4, including a rotational fluid-control valve for selectively actuating the rotation member to move the second rotation member end rotationally in the chosen one of the clockwise and counterclockwise directions.

9. The apparatus of claim 4, an increase of fluid pressure in the member internal volume of the rotation member to a positive rotation fluid pressure, above a resting rotation fluid pressure, causes expansion of the rotation member from a resting configuration to an expanded configuration and movement of the second rotation member end in a selected one of the clockwise and counterclockwise directions, and wherein a decrease of fluid pressure in the member internal volume of the rotation member below the positive rotation fluid pressure causes contraction of the rotation member from the expanded configuration and movement of the second rotation member end in the other one of the clockwise and counterclockwise directions.

10. The apparatus of claim 9, including a controller selectively actuating the second locking mechanism to grasp and release the elongate rod in predetermined coordination with expansion and contraction of the rotation member to and from the expanded configuration to cause predetermined motion of the elongate rod in at least one of the clockwise and counterclockwise directions.

11. The apparatus of claim 1, including a constraining structure associated with at least one of the rotation member and the translation member, to mechanically facilitate the rotational and translational actions of the elongate rod.

12. The apparatus of claim 1, wherein at least one of the second locking mechanism and the first locking mechanism includes two longitudinally extending diaphragms, with the diaphragms arranged in lateral opposition across the elongate rod, the diaphragms being selectively actuable to grasp the elongate rod laterally therebetween.

13. The apparatus of claim 1, wherein the translation member and the rotation member are actuated substantially simultaneously for concurrent longitudinal and rotational movement of the elongate rod.

14. The apparatus of claim 1, wherein the translation member and the rotation member are actuated at different and separate times for sequential longitudinal and rotational movement of the elongate rod.

15. A method of moving an elongate rod relative to a ground surface longitudinally in at least one of a first direction and a second direction, substantially opposite the first direction, and rotationally in at least one of a clockwise and a counterclockwise direction about a longitudinal axis of the elongate rod, the method comprising:
providing a translation member having longitudinally spaced first and second translation member ends;
holding the first translation member end stationary;
permitting the second translation member end to selectively move longitudinally relative to the first translation member end;
providing a first locking mechanism configured for selective longitudinal movement under influence of the second translation member end;
selectively grasping at least a portion of the rod with the first locking mechanism;
actuating the translation member with a translational fluid-control valve to move the second translation member end longitudinally in a chosen one of the first and second directions;
with the actuated translation member, moving the first locking mechanism longitudinally in the chosen one of the first and second directions;
with the first locking mechanism, grasping and releasing at least a portion of the rod in coordination with motion of the first locking mechanism in the chosen one of the first and second directions to move the rod with respect to the ground surface in the chosen one of the first and second directions;
providing a rotation member having longitudinally spaced first and second rotation member ends;
holding the first rotation member end stationary;
permitting the second rotation member end to selectively rotate relative to the first rotation member end;
providing a second locking mechanism configured for selective rotational movement under influence of the second rotation member end;
selectively grasping at least a portion of the rod with the second locking mechanism;
actuating the rotation member with a rotational fluid-control valve to move the second rotation member end rotationally in a chosen one of the clockwise and counterclockwise directions;
with the actuated rotation member, moving the second locking mechanism rotationally in the chosen one of the clockwise and counterclockwise directions;
with the second locking mechanism, grasping and releasing at least a portion of the rod in coordination with motion of the second locking mechanism in the chosen one of the clockwise and counterclockwise directions to move the rod with respect to the ground surface in the chosen one of the clockwise and counterclockwise directions;
selectively controlling a binary on/off actuation of the translational fluid control valve to provide full-step translation control;
selectively controlling a binary on/off actuation of the rotational fluid control valve to provide full-step rotation control;

selectively controlling a valve orifice size of the translational fluid control valve to provide sub-step translation control; and selectively controlling a valve orifice size of the rotational fluid control valve to provide sub-step rotation control.

16. The method of claim 15, wherein actuating the translation member with a translational fluid-control valve to move the second translation member end longitudinally in a chosen one of the first and second directions includes:

selectively increasing fluid pressure in a member internal volume of the translation member to a positive translation fluid pressure, above a resting translation fluid pressure;

responsive to the increase of fluid pressure above the resting translation fluid pressure, expanding the translation member from a resting configuration to an expanded configuration and moving the second translation member end in the first direction;

selectively decreasing fluid pressure in the member internal volume of the translation member below the positive translation fluid pressure; and responsive to the decrease of fluid pressure from the positive translation fluid pressure, contracting of the translation member from the expanded configuration and moving the second translation member end in the second direction.

17. The method of claim 15, wherein actuating the rotation member with a rotational fluid-control valve to move the second rotation member end rotationally in a chosen one of the clockwise and counterclockwise directions includes:

selectively increasing fluid pressure in the member internal volume of the rotation member to a positive rotation fluid pressure, above a resting fluid pressure;

responsive to the increase of fluid pressure to the positive rotation fluid pressure, expanding the rotation member from a resting configuration to an expanded configuration and moving the second rotation member end in a selected one of the clockwise and counterclockwise directions;

selectively decreasing fluid pressure in the member internal volume of the rotation member below the positive rotation fluid pressure; and responsive to the decrease of fluid pressure from the positive rotation fluid pressure, contracting the rotation member from the expanded configuration and moving the second rotation member end in the other one of the clockwise and counterclockwise directions.

18. The method of claim 15, wherein at least one of selectively grasping at least a portion of the rod with the first locking mechanism and selectively grasping at least a portion of the rod with the second locking mechanism includes:

arranging two longitudinally extending diaphragms in lateral opposition across the rod; and selectively actuating both of the diaphragms simultaneously to grasp the elongate rod laterally therebetween.

19. The method of claim 15, wherein moving the first locking mechanism longitudinally in the chosen one of the first and second directions and moving the second locking mechanism rotationally in the chosen one of the clockwise and counterclockwise directions occur substantially simultaneously for concurrent longitudinal and rotational movement of the elongate rod.

20. The method of claim 15, wherein moving the first locking mechanism longitudinally in the chosen one of the first and second directions and moving the second locking mechanism rotationally in the chosen one of the clockwise and counterclockwise directions occur at different and separate times for sequential longitudinal and rotational movement of the elongate rod.

21. An apparatus for moving an elongate rod relative to a ground surface longitudinally in at least one of a first direction and a second direction, substantially opposite the first direction, and rotationally in at least one of a clockwise and a counterclockwise direction about a longitudinal axis of the elongate rod, the apparatus comprising:

an at least partially longitudinally movable translation member having a first translation member end held relatively stationary and a longitudinally spaced second translation member end which is selectively movable longitudinally with respect to the first translation member end via actuation of the translation member, the second translation member end being operatively connected to selectively impart longitudinal motion to the elongate rod; and an at least partially helically twistable rotation member having a first rotation member end held relatively stationary and a longitudinally spaced second rotation member end which is selectively rotatable with respect to the first rotation member end via actuation of the rotation member, the second rotation member end being operatively connected to selectively impart rotational motion to the elongate rod;

wherein the translation member and the rotation member are integrally joined as a single structure at the time the elongate rod is moved.

22. The apparatus of claim 21, wherein the translation member and the rotation member are integrally formed in a single piece as a monolithic structure.

23. The apparatus of claim 21, wherein the translation member and the rotation member both define member internal volumes, the member internal volumes of the translation member and the rotation member being mutually fluidically separated, and wherein fluid is selectively provided to, and removed from, each member internal volume to selectively control fluid pressure in the member internal volumes, wherein changes in fluid pressure in a corresponding member internal volume cause both actuation of the translation member to move the second translation member end longitudinally in the chosen one of the first and second directions, and actuation of the rotation member to move the second rotation member end rotationally in the chosen one of the clockwise and counterclockwise directions.

24. The apparatus of claim 21, wherein the translation member and the rotation member are actuated substantially simultaneously for concurrent longitudinal and rotational movement of the elongate rod.

25. The apparatus of claim 21, wherein the translation member and the rotation member are actuated at different and separate times for sequential longitudinal and rotational movement of the elongate rod.

26. The apparatus of claim 21, including a first locking mechanism selectively movable longitudinally with respect to the ground surface when urged by the second translation member end, the first locking mechanism being configured to selectively grasp at least a portion of the rod.

27. The apparatus of claim 26, including a second locking mechanism, separate from the first locking mechanism, the second locking mechanism being selectively movable rotationally about the longitudinal axis with respect to the ground surface when urged by the second rotation member end, the second locking mechanism being configured to selectively grasp at least a portion of the rod.

28. The apparatus of claim 26, including a third locking mechanism, separate from the first locking mechanism and longitudinally spaced from the first locking mechanism with the rotation member and translation member interposed therebetween, the third locking mechanism applying frictional lateral pressure to at least a portion of the rod, the frictional lateral pressure of the third locking mechanism being configured to permit the rod to move longitudinally under influence of the translation member but to resist longitudinal force of a magnitude less than that applied by the translation member.

29. A system for moving an elongate rod relative to a ground surface longitudinally in at least one of a first direction and a second direction, substantially opposite the first direction, and rotationally in at least one of a clockwise and a counterclockwise direction about a longitudinal axis of the elongate rod, the system comprising an operatively connected plurality of apparatuses according to claim 21.

30. A method of moving an elongate rod relative to a ground surface longitudinally in at least one of a first direction and a second direction, substantially opposite the first direction, and rotationally in at least one of a clockwise and a counterclockwise direction about a longitudinal axis of the elongate rod, the method comprising:
  providing a translation member having longitudinally spaced first and second translation member ends;
  holding the first translation member end stationary;
  permitting the second translation member end to selectively move longitudinally relative to the first translation member end;
  actuating the translation member to move the second translation member end longitudinally in a chosen one of the first and second directions;
  selectively imparting longitudinal motion to the elongate rod via operative connection with the second translation member end;
  providing a rotation member having longitudinally spaced first and second rotation member ends;
  holding the first rotation member end stationary;
  permitting the second rotation member end to selectively rotate relative to the first rotation member end;
  actuating the rotation member to move the second rotation member end rotationally in a chosen one of the clockwise and counterclockwise directions; and
  selectively imparting rotational motion to the elongate rod via operative connection with the second rotation member end.

31. The method of claim 30, wherein actuating the translation member to move the second translation member end longitudinally in a chosen one of the first and second directions includes actuating the translation member with a fluid-control valve to move the second translation member end translationally in a chosen one of the first and second directions;
  wherein actuating the rotation member to move the second rotation member end rotationally in a chosen one of the clockwise and counterclockwise directions includes actuating the rotation member with a fluid-control valve to move the second rotation member end rotationally in a chosen one of the clockwise and counterclockwise directions;
  the method including:
  selectively controlling a binary on/off actuation of the translational fluid control valve to provide full-step translation control;
  selectively controlling a binary on/off actuation of the rotational fluid control valve to provide full-step rotation control;
  selectively controlling a valve orifice size of the translational fluid control valve to provide sub-step translation control; and
  selectively controlling a valve orifice size of the rotational fluid control valve to provide sub-step rotation control.

32. The method of claim 30, wherein actuating the translation member to move the second translation member end longitudinally in a chosen one of the first and second directions includes:
  selectively increasing fluid pressure in a member internal volume of the translation member to a positive translation fluid pressure, above a resting translation fluid pressure;
  responsive to the increase of fluid pressure above the resting translation fluid pressure, expanding the translation member from a resting configuration to an expanded configuration and moving the second translation member end in the first direction;
  selectively decreasing fluid pressure in the member internal volume of the translation member below the positive translation fluid pressure; and
  responsive to the decrease of fluid pressure from the positive translation fluid pressure, contracting the translation member from the expanded configuration and moving the second translation member end in the second direction.

33. The method of claim 30, wherein actuating the rotation member with a fluid-control valve to move the second rotation member end rotationally in a chosen one of the clockwise and counterclockwise directions includes:
  selectively increasing fluid pressure in the member internal volume of the rotation member to a positive rotation fluid pressure, above a resting fluid pressure;
  responsive to the increase of fluid pressure to the positive rotation fluid pressure, expanding the rotation member from a resting configuration to an expanded configuration and moving the second rotation member end in a selected one of the clockwise and counterclockwise directions;
  selectively decreasing fluid pressure in the member internal volume of the rotation member below the positive rotation fluid pressure; and
  responsive to the decrease of fluid pressure from the positive rotation fluid pressure, contracting the rotation member from the expanded configuration and moving the second rotation member end in the other one of the clockwise and counterclockwise directions.

34. The method of claim 30, wherein at least one of selectively imparting longitudinal motion to the elongate rod via operative connection with the second translation member end and selectively imparting rotational motion to the elongate rod via operative connection with the second rotation member end includes:
  arranging two longitudinally extending diaphragms in lateral opposition across the rod to form a locking mechanism operatively connected with at least one of the second translation member end and the second rotation member end; and
  selectively actuating both of the diaphragms simultaneously to grasp the elongate rod laterally therebetween.

35. The method of claim 30, wherein selectively imparting longitudinal motion to the elongate rod and selectively imparting rotational motion to the elongate rod occur substantially simultaneously for concurrent longitudinal and rotational movement of the elongate rod.

36. The method of claim 30, wherein selectively imparting longitudinal motion to the elongate rod and selectively imparting rotational motion to the elongate rod occur at different and separate times for sequential longitudinal and rotational movement of the elongate rod.

37. The method of claim 30, including:
providing a first locking mechanism configured for selective longitudinal movement under influence of the second translation member end;
selectively grasping at least a portion of the rod with the first locking mechanism;
with the actuated translation member, moving the first locking mechanism longitudinally in the chosen one of the first and second directions;
with the first locking mechanism, grasping and releasing at least a portion of the rod in coordination with motion of the first locking mechanism in the chosen one of the first and second directions to move the rod with respect to the ground surface in the chosen one of the first and second directions.

38. The method of claim 37, including:
providing a second locking mechanism configured for selective rotational movement under influence of the second rotation member end;
selectively grasping at least a portion of the rod with the second locking mechanism;
actuating the rotation member with a fluid-control valve to move the second rotation member end rotationally in a chosen one of the clockwise and counterclockwise directions;
with the actuated rotation member, moving the second locking mechanism rotationally in the chosen one of the clockwise and counterclockwise directions;
with the second locking mechanism, grasping and releasing at least a portion of the rod in coordination with motion of the second locking mechanism in the chosen one of the clockwise and counterclockwise directions to move the rod with respect to the ground surface in the chosen one of the clockwise and counterclockwise directions.

39. The method of claim 37, including:
providing a third locking mechanism, separate from the first locking mechanism and longitudinally spaced from the first locking mechanism with the rotation member and translation member interposed therebetween;
with the third locking mechanism, applying frictional lateral pressure to at least a portion of the rod; and
with the frictional lateral pressure of the third locking mechanism, permitting the rod to move longitudinally under influence of the translation member but resisting longitudinal force of a magnitude less than that applied by the translation member.

* * * * *